US012226145B2

(12) United States Patent
Batchelor et al.

(10) Patent No.: US 12,226,145 B2
(45) Date of Patent: *Feb. 18, 2025

(54) COMBINATION ELECTROSURGICAL INSTRUMENT (71) Applicant: GYRUS ACMI, INC., Westborough, MA (US)

(72) Inventors: Kester Julian Batchelor, Mound, MN (US); Eric G. Tate, Maple Grove, MN (US); Huisun Wang, Maple Grove, MN (US); Riyad Moe, Madison, WI (US)

(73) Assignee: Gyrus ACMI, Inc., Westborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/399,130

(22) Filed: Dec. 28, 2023

(65) Prior Publication Data
US 2024/0148431 A1 May 9, 2024

Related U.S. Application Data (63) Continuation of application No. 16/096,440, filed as application No. PCT/US2016/035986 on Jun. 6, 2016, now Pat. No. 11,890,049.

(51) Int. Cl.
*A61B 17/285* (2006.01)
*A61B 17/295* (2006.01)
(Continued)

(52) U.S. Cl.
CPC ........ *A61B 18/1442* (2013.01); *A61B 17/285* (2013.01); *A61B 17/295* (2013.01);
(Continued)

(58) Field of Classification Search
CPC .............. A61B 17/285; A61B 18/1442; A61B 2018/1412; A61B 2018/1462; A61B 2217/005; A61B 2218/002
See application file for complete search history.

(56) References Cited

U.S. PATENT DOCUMENTS 4,340,369 A 7/1982 Steiner et al.
5,007,827 A 4/1991 Difranco
(Continued)

FOREIGN PATENT DOCUMENTS

WO WO-2017213619 A1 12/2017

OTHER PUBLICATIONS

"Animation demonstrating transcollation technology from Medtronic advanced energy", accessed Mar. 4, 2016 <https://vimeo.com/33665262PTB_iframe=true&height=323&width=480>.
(Continued)

*Primary Examiner* — Joseph A Stoklosa
*Assistant Examiner* — Annie L Shoulders
(74) *Attorney, Agent, or Firm* — Schwegman Lundberg & Woessner, P.A.

(57) ABSTRACT

An instrument including a first arm, a second arm, and a blade. The first arm includes a lumen in communication with a source of irrigation fluid and one or more outlets in communication with the lumen for delivering the irrigation fluid to a surgical site. The instrument is switchable between a first configuration and a second configuration. In the first configuration, the instrument is configured to deliver a first therapy current through a distal end of the first arm, a distal end of the second arm, or both. In the second configuration, a distal end of the blade extends beyond the distal end of the first arm and beyond the distal end of the second arm.

20 Claims, 7 Drawing Sheets

(51) Int. Cl.
- *A61B 18/12* (2006.01)
- *A61B 18/14* (2006.01)
- *A61B 17/30* (2006.01)
- *A61B 17/3211* (2006.01)
- *A61B 18/00* (2006.01)

(52) U.S. Cl.
CPC ........ *A61B 18/14* (2013.01); *A61B 2017/305* (2013.01); *A61B 2017/32113* (2013.01); *A61B 2018/00029* (2013.01); *A61B 2018/00077* (2013.01); *A61B 2018/00083* (2013.01); *A61B 2018/00166* (2013.01); *A61B 2018/00196* (2013.01); *A61B 2018/00607* (2013.01); *A61B 2018/1253* (2013.01); *A61B 2018/126* (2013.01); *A61B 2018/1412* (2013.01); *A61B 2018/1455* (2013.01); *A61B 2018/1462* (2013.01); *A61B 2217/005* (2013.01); *A61B 2217/007* (2013.01); *A61B 2218/002* (2013.01); *A61B 2218/007* (2013.01)

(56) References Cited

U.S. PATENT DOCUMENTS

| | | | |
|---|---|---|---|
| 5,269,782 | A | 12/1993 | Sutter |
| 6,036,700 | A | 3/2000 | Stefanchik et al. |
| 6,558,385 | B1 | 5/2003 | Mcclurken et al. |
| 6,863,669 | B2 | 3/2005 | Spitzer |
| 6,899,712 | B2 | 5/2005 | Moutafis et al. |
| 7,604,635 | B2 | 10/2009 | Mcclurken et al. |
| 7,901,403 | B2 | 3/2011 | Woloszko et al. |
| 8,361,068 | B2 | 1/2013 | Mcclurken |
| 8,870,864 | B2 | 10/2014 | Davison et al. |
| 8,882,756 | B2 | 11/2014 | Greeley et al. |
| 9,023,035 | B2 | 5/2015 | Allen, IV et al. |
| 9,173,698 | B2 | 11/2015 | Van Lue et al. |
| 9,358,065 | B2 | 6/2016 | Ladtkow et al. |
| 11,890,049 | B2 * | 2/2024 | Batchelor ............ A61B 17/285 |
| 2003/0216733 | A1 | 11/2003 | Mcclurken et al. |
| 2009/0186316 | A1 | 7/2009 | Hahn |
| 2012/0095458 | A1 | 4/2012 | Cybulski et al. |
| 2014/0188105 | A1 | 7/2014 | Conley et al. |
| 2014/0249547 | A1 | 9/2014 | Boone, III |
| 2014/0276795 | A1 | 9/2014 | Batchelor et al. |
| 2015/0223862 | A1 | 8/2015 | Allen, IV et al. |
| 2015/0282873 | A1 | 10/2015 | Batchelor et al. |
| 2016/0051314 | A1 | 2/2016 | Batchelor et al. |
| 2016/0128708 | A1 | 5/2016 | Mikus et al. |
| 2016/0143657 | A1 | 5/2016 | Estera et al. |
| 2017/0224348 | A1 | 8/2017 | Wong et al. |
| 2019/0142502 | A1 | 5/2019 | Batchelor et al. |

OTHER PUBLICATIONS

"U.S. Appl. No. 16/096,440, Final Office Action mailed Nov. 26, 2021", 19 pgs.

"U.S. Appl. No. 16/096,440, Final Office Action mailed Dec. 13, 2022", 21 pgs.

"U.S. Appl. No. 16/096,440, Non Final Office Action mailed May 24, 2021", 21 pgs.

"U.S. Appl. No. 16/096,440, Non Final Office Action mailed May 24, 2022", 20 pgs.

"U.S. Appl. No. 16/096,440, Notice of Allowance mailed Sep. 27, 2023", 8 pgs.

"U.S. Appl. No. 16/096,440, Preliminary Amendment filed Oct. 25, 2018", 8 pgs.

"U.S. Appl. No. 16/096,440, Response filed Feb. 24, 2022 to Final Office Action mailed Nov. 26, 2021", 15 pgs.

"U.S. Appl. No. 16/096,440, Response filed Mar. 10, 2023 to Final Office Action mailed Dec. 13, 2022", 16 pgs.

"U.S. Appl. No. 16/096,440, Response filed Aug. 24, 2021 to Non Final Office Action mailed May 24, 2021", 14 pgs.

"U.S. Appl. No. 16/096,440, Response filed Aug. 24, 2022 to Non Final Office Action mailed May 24, 2022", 15 pgs.

"International Application Serial No. PCT/US2016/035986, International Preliminary Report on Patentability mailed Dec. 20, 2018", 15 pgs.

"International Application Serial No. PCT/US2016/035986, International Search Report mailed Mar. 15, 2017", 5 pgs.

"International Application Serial No. PCT/US2016/035986, Written Opinion mailed Mar. 15, 2017", 13 pgs.

"Medtronic Advanced energy webpage", accessed Mar. 4, 2016 <http//www.medtronics.com/for-healthcare-professionals/business-unit-landing~page/medtronics-advanced-energy/index.htm>.

"Medtronic Aquamantys System overview webpage", accessed Mar. 4, 2016 <http://www.medtronic.com/for-healthcare-professionals/products-therapies/orthopaedic/electrosurgical-products/aquamantys-system-sealers/index.htm>.

\* cited by examiner

COMBINATION ELECTROSURGICAL INSTRUMENT

CROSS-REFERENCE TO RELATED APPLICATIONS

This application is a Continuation of U.S. patent application Ser. No. 16/096,440, filed Oct. 25, 2018, now issued as U.S. Pat. No. 11,890,049, which is a U.S. National Stage filing under 37 U.S.C. § 371 from International Application of PCT/US2016/035986, filed Jun. 6, 2016, the contents of which are hereby incorporated by reference in their entireties.

FIELD

These teachings relate to an instrument for effecting an object or anatomical feature.

BACKGROUND

Various instruments for use in medical procedures are known; however, instrument improvements are always desired.

Some instruments are used to cut an anatomical feature; and after cutting, other instruments are used to coagulate a bleeding anatomical feature. As can be imagined, time and focus is lost between switching instruments to cut and then coagulate an anatomical feature. It may therefore be desirable to combine cutting and coagulating capabilities into a single instrument to reduce the number of instrument swaps required during a medical procedure.

Some instruments, such as an energized scalpel, can provide a single electrosurgical modality, either a monopolar therapeutic current for cutting and coagulating an anatomical feature. Other energized instruments can provide a bipolar therapeutic current for coagulating and sealing an anatomical feature. Similarly, time and focus is lost between switching instruments when a monopolar therapeutic current is desired over a bipolar therapeutic current, or vice versa. It may therefore be desirable to have a reconfigurable electrosurgical instrument or scalpel that has both monopolar and bipolar therapeutic capabilities. Further specialized instruments provide an output for precoagulating the tissue, sealing small vessels within the tissue structure so that subsequent cutting of the tissue with a scalpel or energized scalpel are less likely to result in bleeding.

Some instruments used for coagulating an anatomical feature such as tissue can cause a significant temperature increase in the tissue, which may undesirably lead to tissue desiccation, tissue sticking, tissue perforation, char formation, and/or smoke generation. It may therefore be desirable to provide an instrument that can reduce or inhibit tissue desiccation, tissue sticking, tissue perforation, char formation, and/or smoke generation.

Some instruments, such as forceps, are user activated and require pressure application on one or more arms of the forceps to capture, grip, and/or grasp, an anatomical feature located between the arms. Releasing the pressure on one or both of the arms causes the arms to open thus releasing the anatomical feature from between the arms. The pressure applied to the arms is usually applied via finger pressure, which may cause fatigue especially during prolonged medical procedures. It may therefore be desirable to provide an instrument that can be used to capture, grip, and/or grasp an anatomical feature without requiring applying pressure to one or both of the arms, thus relieving user fatigue.

Some examples of instruments are disclosed in U.S. Pat. Nos. 9,023,035, 8,882,756, and 6,929,641; US Patent App. Pub. Numbers 2015/0223862 and 2014/0276795; and in U.S. patent application Ser. No. 14/672,525, the disclosures of which are hereby incorporated by reference herein for all purposes.

SUMMARY

These teachings provide an instrument that has both cutting and coagulating capabilities. The instrument is reconfigurable so that one or more features of the instrument can be moved or repositioned.

These teachings provide a reconfigurable electrosurgical instrument, such as a scalpel, that has both monopolar and bipolar therapeutic capabilities.

These teachings provide an instrument that can reduce or inhibit tissue desiccation, tissue sticking, tissue perforation, char formation, and smoke generation.

These teachings also provide an instrument that can be used to capture, grip, and/or grasp an anatomical feature without causing user fatigue by allowing the arms of the instrument to close by releasing pressure applied to the arms.

These teachings provide an instrument that can precoagulate tissue allowing subsequent resection or cutting with a reduced amount of bleeding, where the cutting or resection element is incorporated into the same device and is switchable between a first configuration and a second configuration.

Further yet, these teachings provide an instrument comprising a first arm, a second arm, and a blade. The first arm comprises a lumen in communication with a source of irrigation fluid and one or more outlets in communication with the lumen for delivering the irrigation fluid to a surgical site. The instrument is switchable between a first configuration and a second configuration. In the first configuration, the instrument is configured to deliver a first therapy current through a distal end of the first arm, a distal end of the second arm, or both. In the second configuration, a distal end of the blade extends beyond the distal end of the first arm and beyond the distal end of the second arm.

Still further yet, these teachings provide an instrument comprising a first scalpel, a second scalpel, a first insulator, and a second insulator. The first scalpel comprises a first electrode and a second electrode. The second scalpel is located between the first electrode and the second electrode. The first insulator is located between the first electrode and the second scalpel so that the first electrode and the second scalpel are electrically insulated from each other. The second insulator is located between the second electrode and the second scalpel so that the second electrode and the second scalpel are electrically insulated from each other. The instrument is switchable between a first configuration and a second configuration. In the first configuration, the second scalpel is retracted so that a distal end of the second scalpel does not extend beyond a distal end of the first scalpel, and the instrument is configured to deliver a first therapy current through the first arm, the second arm, or both. In the second configuration, the second scalpel extends beyond a distal end of first electrode and a distal end of the second electrode.

These teachings provide an instrument comprising a forceps comprising a first arm, a second arm, and a moveable blade. The first arm having a first gripper. The second arm having a second gripper. The first arm and the second arm cross over one another. The instrument is switchable between a first configuration and a second configuration. In the first configuration, the instrument is configured to deliver a first therapy current through the first arm, the second arm, or both, and the blade is fie from extending beyond a distal end of the first arm and a distal end of the second arm. In the second configuration, the blade extends beyond the distal end of the first arm and the distal end of the second arm.

DETAILED DESCRIPTION

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

These teachings provide an instrument. The instrument may be a medical instrument. The instrument may be any instrument or device for effecting an object or anatomical feature. Effecting may mean, for example, holding, manipulating, engaging, moving, grasping, gripping, constricting, pushing, pulling, cutting, tearing, coagulating, sealing, cauterizing, dissecting, fulgurating, or a combination thereof an object or anatomical feature. The anatomical feature may be any anatomical feature, such as a vessel, tissue, vein, artery, the like, or a combination thereof. The instrument can be used in virtually any procedure, medically related or other. In medical procedures, the instrument can be used in open procedures, laparoscopic procedures, or both. The instrument can be used in orthopedic procedures, spinal procedures, general procedures, cardiovascular procedures and/or neurological procedures. The instrument may be any instrument or device having one or more arms. The instrument may be a forceps. The instrument may not be a forceps or may be free of forceps and/or forceps arms. The forceps can be virtually any forceps known in the field. The instrument may be a tweezers. The instrument may be a cross tweezers. The instrument can be a scalpel having one or more scalpels. The instrument can be used with or without power. When used with power, the instrument can be an electrosurgical instrument.

One or more electrical currents, therapies, and/or signals may be provided to the instrument. The power, the one or more electrical currents, therapies, and/or signals may be provided to the instrument via a power source. The power source may be any suitable power source. The power source may be a generator. The power source may be of the type described in U.S. Pat. No. 7,282,048B2, the teachings of which are hereby incorporated by reference herein for all purposes. The one or mom electrical currents, therapies, and/or signals may be provided to, through, and/or between one or more active portions, one or more arms, one or more electrodes, one or more blades, one or more scalpels, one or more gripping portions, a remote electrode or patient pad, or a combination thereof.

The one or more electrical currents, therapies, and/or signals provided by the power source may be monopolar energy, bipolar energy, a blended energy, or a combination thereof. The one or more electrical currents, therapies, and/or signals may include a cut waveform, a coagulation waveform, and/or a blended waveform. During use, an electrical circuit may be completed by passing monopolar energy or current from the power source to one or more arms, one or more electrodes, one or more blades, one or more scalpels, one or more active portions, or a combination thereof, to anatomical feature, and then to a remote electrode or patient pad. During use, an electrical circuit may be completed by passing bipolar energy or current from the power source to an active electrode or an active feature of one or more arms, one or more electrodes, one or more blades, one or more scalpels, or a combination thereof, through the anatomical feature, and to a return electrode or active portion of one or more arms, one or more electrodes, one or more blades, one or more scalpels, or a combination thereof. A cut waveform energy or therapy signal may be delivered from the power source to the instrument, and can be described as a higher current/lower voltage waveform compared to a coagulation waveform energy or therapy signal. The coagulation waveform energy or therapy signal may be modulated or interrupted from the power source to the instrument, and can be described as a lower current/higher voltage waveform compared to the cut waveform. The blended waveform may be a combination of a cut waveform and a coagulation waveform. The blended waveform may advantageously allow a user to coagulate the object or anatomical feature while also cutting the object or anatomical feature. The blended waveform may be of the type described in the above-mentioned U.S. Pat. No. 7,282,048B2.

Generally speaking, the instrument according to the teachings herein may be configured and/or operable to allow a user to paint tissue with one or more therapy currents and irrigation fluid and then switch to a monopolar, bipolar, or non-electrosurgical blade to cut the pre-coagulated anatomical feature. Alternatively, the instrument can be used to coagulate an anatomical feature once cutting has been performed to seal the anatomical feature. The instrument may provide a combination of therapeutic currents or energy and irrigation fluid that provides hemostatic sealing of soft tissue and bone during surgery.

The instrument may be in communication with a fluid source. The source may supply irrigation fluid to the instrument. The irrigation fluid may be provided to clean a distal end of the instrument, clean a feature of interest, clean a surgical site, or a combination thereof. The irrigation fluid may be a conductive fluid that may function to electrically conduct the one or more electrical therapies or signals. The irrigation fluid may be saline. The irrigation fluid may be non-conductive. Non-conductive fluid may be less preferred than a conductive fluid, however, the use of a non-conductive fluid may provide certain advantages over the use of a conductive fluid, which may include reducing the occurrence of tissue sticking to the electrode and cooling of the electrode and/or tissue. An example of non-conductive irrigation fluid is deionized water.

The fluid source may supply suction to the instrument. That is, a single line, or another line in communication with the fluid source may supply suction to the instrument. The suction may function to evacuate fluid from a surgical site. For example, the suction may function to remove smoke, air, or both from the feature of interest. The same fluid source may provide both the irrigation fluid and the suction, or the irrigation may be provided by one fluid source and the suction or fluid evacuation may be provided by another fluid source. The irrigation fluid and the suction can be provided to the instrument at the same time or at different times (e.g., first irrigation fluid and then suction, or vice versa).

The instrument may include an effector. The effector may function to effect an object or anatomical feature. For example, the effector may permit holding, manipulating, engaging, moving, grasping, gripping, constricting, pushing, pulling, cutting, tearing, coagulating, sealing, cauterizing, dissecting, fulgurating, or a combination thereof an object or anatomical feature. The effector may include one or more features of a forceps, a tweezers, a scalpel, an electrode or a combination thereof. The effector may include one or more of the arms, blades, scalpels, electrodes, insulators, or a combination thereof described herein.

The instrument, the effector, the one or more of the arms, blades, scalpels, electrodes, insulators, or a combination thereof may be moveable or reconfigurable relative to a frame of reference. The frame of reference may be any suitable reference point, plane, axis, and/or feature. For example, the frame of reference may be one or more arms, an opposing arm, a blade, one or more of the scalpels, an opposing scalpel, one or more electrodes, a user, a patient, a surgical site, the anatomy, or a combination thereof.

The instrument, the effector, or both may be operable in one or more configurations. The instrument, the effector, the one or more of the arms, blades, scalpels, electrodes, insulators, or a combination thereof may be moveable or reconfigurable between two or more configurations. The instrument, the effector, the one or more of the arms, blades, scalpels, electrodes, insulators, or a combination thereof may be moveable or reconfigurable between a first configuration and a second configuration. As used herein, either the first configuration or the second configuration may be the steady state configuration.

In the first configuration, the second configuration, or both, the first arm, the second arm, or both may be moved towards or away from a centrally located blade. In the first configuration, the second configuration, or both, a blade or scalpel may extend beyond a distal end of a first electrode, arm and/or scalpel and a distal end of a second electrode, arm, and/or scalpel. In the first configuration, the second configuration, or both, a blade or scalpel may not extend or may free from extending beyond a distal end of a first electrode, arm and/or scalpel and a distal end of a second electrode, arm, and/or scalpel.

The first configuration, the second configuration, or both may be a monopolar electrosurgical configuration, a bipolar electrosurgical configuration, or both. In the first configuration, the second configuration, or both, a suitable therapy current (e.g., a monopolar signal or therapy or a bipolar therapy signal or therapy) may be delivered from the power source to or through one or more blades, arms, scalpels, electrodes, active portions, or a combination thereof. In the first configuration, the second configuration, or both, a suitable therapy current may be delivered from the power source between two or more of the following: blades, arms, scalpels, electrodes, active portions, a remote electrode or patient pad, or a combination thereof.

In the first configuration, the second configuration, or both, a suitable therapy current may be prevented from passing or being delivered from the power source and one or more of the following: blades, arms, scalpels, electrodes, active portions, a remote electrode or patient pad, or a combination thereof.

The instrument may be operable in a simultaneous configuration which comprises any of the first configurations and the second configuration described herein. In a simultaneous configuration, a first therapy current can be passed between a first arm and a second arm while at the same time a second therapy current is passed from the blade to a remote electrode or patent pad. In a simultaneous configuration, a first therapy current can be passed between a first arm and a second arm and then a second therapy current can be passed from the blade to a remote electrode while the first therapy current is free from passing between the first arm and the second arm.

The instrument, the effector, or both may include one or more arms. The one or more arms may be configured to and/or may function to effect an object or anatomical feature. The one or more arms may function to deliver one or more therapeutic currents or signals, irrigation fluid, suction, or a combination thereof to a surgical site or anatomical feature. The one or more arms may function to remove heat from a surgical site or anatomical feature. The one or more arms may be free of gripping devices and/or features for grasping and/or gripping an anatomical feature. For example, the one or more arms may not be a forceps and/or arms of a forceps.

One or more of the arms may be moveable or reconfigurable. Moveable or reconfigurable may mean that the position of one or more of the arms can be changed. Moveable or reconfigurable may mean that one or both of the arms can be moved or extended away from a hand piece of the instrument, a surgeon or operator using the instrument, one or more other arms, blades, electrodes, or a combination thereof. Moveable or reconfigurable may mean that one or more of the arms can be moved or extended towards a patient or surgical site. Moveable may mean that one or both of the arms can be retracted or moved towards a hand piece, a surgeon or operator using the instrument, one or more other arms, blades, electrodes, or a combination thereof. Moveable or reconfigurable may mean that one or more of the arms can be vertically moved relative to one or more other arms, blades, electrodes, or a combination thereof (e.g., moveable or reconfigurable up and down). Moveable or reconfigurable may mean that one or more of the arms are laterally moveable or displaceable towards or away from one or more other arms, blades, electrodes, or a combination thereof (e.g., moveable or reconfigurable side to side). Moveable or reconfigurable may mean that one or more of the arms can be diagonally or along a path that is irregular (e.g., non-linear) relative to one or more other arms, blades, electrodes, or a combination thereof (e.g., moveable or reconfigurable up and down). Moveable or reconfigurable may mean that one or more of the arms are rotatable about their longitudinal axis. Moveable or reconfigurable may mean any combination of arm movements described herein.

In some configurations, the arms may be static (e.g., not moveable). In some configurations the arms may be spaced apart and/or held at a fixed distance apart suitable for painting a site of interest with RF energy or a suitable therapy current to electrically effect an anatomical feature. The one or more arms may be electrically conductive and/or may include one or more electrodes or active portions so that a therapy current can be passed from a power source to, from and/or between the one or more arms, electrodes, blades, scalpels, remote electrodes, or a combination thereof. The one or more electrodes or active portions may be located at or near a distal end of the corresponding one or more arms.

The one or more arms may be made of a suitable material for use in medical procedures. For example, the one or more arms may be made of steel, stainless steel, carbon steel, or a combination thereof. Each of the one or more arms may include a material with a thermal conductivity and the thermal conductivity of the arms may be the same; one arm may be higher than the other working arm; or both. The one or more arms may include one or more materials along the length of the working arm. For example, the arms may be entirely made of stainless steel. Preferably, each arm includes two or more materials. For example, the arms may have a base material of stainless steel and the working arms may be coated with an insulating material such as silicone or polytetrafluoroethylene (PTFE). The one or more arms may include any material that is safe for use in a surgical procedure, and preferably in an electrosurgical procedure. The one or more arms may include metals, plastics, a polymer, an elastomer, gold, silver, copper, titanium, aluminum, iron based metals, stainless steel, silicone, polytetrafluoroethylene (PTFE), insulating polymers, rubber, or a combination thereof. Preferably, each arm is substantially coated with an insulating material except for a contact region between the two working arms where the working arms contact each other. The one or more arms may be coated in regions where the user contacts the arms. The one or more arms may include an insulating material where the arms contact a blade electrode so that heat from the blade electrode is not transferred to the arms. The material of the arms, a coating on the arms, a housing of the arms, or a combination thereof may prevent a dissipation of heat from the arms. The one or more arms may be insulated from the blade so that thermal energy or electrical energy is prevented from being transferred to the arms (e.g., the blade, arms, or both may include an insulating coating).

The one or more arms are made from a material that can withstand repeated sterilization in high-temperature autoclaves. However, the arms may also be made of material suitable to be used once and then discarded, such as plastic, for example.

The one or more arms may be substantially straight; may include one or more angles, bends or arcs; or a combination thereof. The one or more arms may be substantially rigid; substantially flexible; substantially resilient; or a combination thereof. The one or more arms may be malleable or reconfigurable so that at least a portion of the arm can be manually shaped, bent, and/or distorted by a user.

As used herein, the one or more scalpels, blades, and arms may include one or more active portions and one or more inactive portions. The one or more active portions may be any portion that supplies or conducts power, signals, current, or a combination thereof. The one or more active portions may be substantially surrounded by inactive portions or portions that are insulated. The inactive portion may be any portion that does not supply power, that is insulated, or both. The inactive portion may be any portion that may prevent a transfer of power through incidental contact and thus are insulated so that an incidental transfer of power does not occur. For example, an outside of the arms, blades, scalpels, electrodes, or a combination thereof may be coated with an insulating material so that if the arms, blades, scalpels, electrodes accidentally contact tissue proximate to the tissue of interest the proximate tissue is not subjected to a transfer of power. The inactive portion and the active portion may be made of different materials, coated with different materials, or both.

The one or more arms may include one or more lumen. The one or more lumen may function to provide or define a conduit or passageway. The one or more lumen may function to provide a conduit or passageway for allowing irrigation fluid, suction, or both to pass from one or more sources to a surgical site or anatomical feature. The one or more lumen may function to provide for a heat pipe to remove heat from a surgical site and/or region of a corresponding arm.

The one or more arms may include any number of lumen. For example, the one or more arms may together or individually include one or more lumen for delivering irrigation fluid from one or more sources to a surgical site; one or more lumen for delivering suction from one or more sources to a surgical site; one or more lumen functioning as a heat pipe; or a combination thereof. For example, one arm can have one or more lumen with outlets to allow irrigation fluid and/or suction to exit and one or more sealed lumen functioning as a heat pipe within the same arm. In some configurations, one or more of the arms may be free of lumen. For example, it may be desirable in some configurations for an arm to be made of a suitable solid material.

The one or more arms may include one or more outlets. The one or more outlets may function to provide for the irrigation fluid and/or suction to be passed and/or delivered from the corresponding lumen to a surgical site. The one or more outlets may be any suitable size. The one or more arms may comprise any number of outlets. The one or more outlets may be located at or near a distal end of a respective arm. The one or more outlets may face forward from a distal end; may face laterally from a distal end; or both. The one or more outlets may face laterally inwards (e.g., towards a blade and/or one or more other arms). The one or more outlets may face laterally outwards (e.g., away from a blade and/or one or more other arms). One or both of the arms may include one or more outlets that face any direction described herein.

The instrument, the effector, the one or more arms, or a combination thereof may include one or more heat pipes. The heat pipe may function to transfer heat from a region of a greater concentration of heat to a region with a lower concentration of heat. The heat pipe may function to carry heat from a first location to a second location where the heat is dissipated. The heat pipe may carry heat from a distal end of the instrument, arm, or both to a proximal end (i.e., an end of the instrument and/or arm closest to the user), a central portion (e.g., a portion of the arm between the distal end and the proximal end), or a combination of both of the instrument, the arms, or both. The heat pipe may be connected to one or more electrodes of a corresponding arm, blade, scalpel, or a combination thereof. The heat pipe may be located in a portion of the one or more arms that become heated so that heat is transferred from the arms to the heat pipe. The heat pipe may be located in a corresponding lumen in the one or more arms. The one or more heat pipes may be hermetically sealed, self-contained, a partial vacuum, or a combination thereof. The one or more heat pipes may include a fluid to absorb heat, transport heat, reject heat, dissipate heat, or a combination thereof. The fluid may be located in a heat pipe located in a lumen, or the fluid may be located in the lumen. The one or more heat pipes may be filled with water, alcohol, sodium, ammonia, ethanol, methanol, or other suitable fluid. The fluid may undergo one or more phase changes and preferably two or more phase changes (e.g., evaporation, condensation, or both) that assist in removing heat from the arms, the electrosurgical device, or both. The fluid may assist in transporting heat from a first end of the heat pipe to a second end of the heat pipe; the first end may be a higher temperature than the second end. The first end may be a distal end and the second end may be a proximal end, or vice versa. The one or more heat pipes may function so that a fluid sealed within the heat pipe when heated evaporates from the distal end and moves to the proximal end where the fluid condenses and releases the heat. The heat may be removed via one or more heat sinks at a proximal end of the arm or heat pipe. The condensate then moves from the proximal end back to the distal end and the cycle repeats.

The heat pipe may be sufficiently long and/or have a sufficiently large cross-sectional thickness (e.g., diameter) so that fluid travels from the distal end of the heat pipe to the proximal end of the heat pipe so that the fluid is cooled. The heat pipe may be sufficiently long and/or have a sufficient cross-sectional thickness so that evaporated fluid travels from the hot end of the heat pipe (e.g., distal end) to the cool end of the heat pipe (e.g., proximal end) where the fluid condenses. The heat pipe may be sufficiently long and/or have a sufficient cross-sectional thickness so that the proximal end remains sufficiently cool so that the evaporated fluid condenses. The length and/or cross-sectional thickness may be sufficiently large so that the heat pipe continues to cool over an extended duration of use (e.g., about 10 minutes or more, about 20 minutes or more, about 30 minutes or more, or even about 1 hour or more of substantially continuous use). The fluid when condensed may travel from the cool end to the hot end via capillary action, centrifugal force, gravity, or a combination thereof. The heat pipe may include a sufficient amount of fluid so that the heat pipe substantially maintains a constant temperature of the working arms, the electrosurgical device, or both for the duration of use. The heat pipe may include a sufficient amount of fluid so that the temperature of the heat pipe raises by a temperature of about 40° C. or less, about 30° C. or less, about 20° C. or less, or about 10° C. or less over the duration of use, over an extended duration of use, or both. Each of the one or more heat pipes may be connected to one or more heat sinks.

The instrument, the effector, the arms, the heat pipes or a combination thereof may include one or more heat sinks. The one or more heat sinks may be connected to the one or more heat pipes or arms. Each heat pipe may be connected to a heat sink, have an integral heat sink, or both. The heat pipes may extend through the heat sinks and the heat sinks may remove heat from the heat pipe or arm through thermal contact. The heat pipe may transfer heat to the heat sink via a heat transfer medium (e.g., a thermal paste) so that heat is transferred from the heat pipe to the heat sink. The heat sink and the heat pipes may be made of the same material. The heat sink may be an extended portion of the heat pipe or arm that acts to dissipate heat. For example, a coil, fin or other extended shape may extend from an end of the heat pipe or arm and may allow for heat transfer. The heat sink may be located on the "cold end" or evaporation end of the heat pipe, on the proximal end of the heat pipe, the proximal end of the arms, the proximal end of the instrument, or a combination thereof. The heat sink may increase the surface area of each of the one or more heat pipes. The heat sink may include one or more heat exchange surfaces that transfers heat into the surrounding environment or ambient cooling fluid, such as room air for example. The surface area of the heat sink surface may be about two times or more, about three times or mow, or even about four times or more than the surface area of the heat pipe. The heat sink may be and/or include fins, baffles, an increase in surface area, tubes, plates, ribs, or a combination thereof. The heat sink may be an integral part of the arms so that movement of the arms moves the heat sink or vice versa. The heat sink, heat pipe, or both may be partially and or entirely shielded from contact by the user so that heat from the heat pipe, the heat sink, or both does not directly contact the user. The heat sink may be made of the same material as the heat pipe. The heat sink may be made of a material with high conductivity, higher conductivity than the heat pipe, or both. The heat sink may use natural convection, forced convection, or both to dissipate heat. Movement of the instrument during use may force air over the heat sink, the heat exchange surface, or both and transfer heat into the surrounding environment. The heat sink may be connected to or may include an active circuit element such as a Peltier chip. When power is applied to a Peltier chip, heat may move from one side to the other, so that one side gets cooler while the other gets hotter. The "hot side" may be connected to a heat sink to transfer heat to the surrounds so that the "hot side" remains at ambient temperature, while the cool side goes below an ambient temperature of the surroundings. The heat sink may be connected to or may include a motor cooling system that uses suction to draw in ambient air and pass the ambient air over a housing such as disclosed in Applicant's commonly owned US Patent Application Publication No. US 2016-0081699, the disclosure of which is hereby incorporated by reference in its entirety for all purposes.

Figure 9:
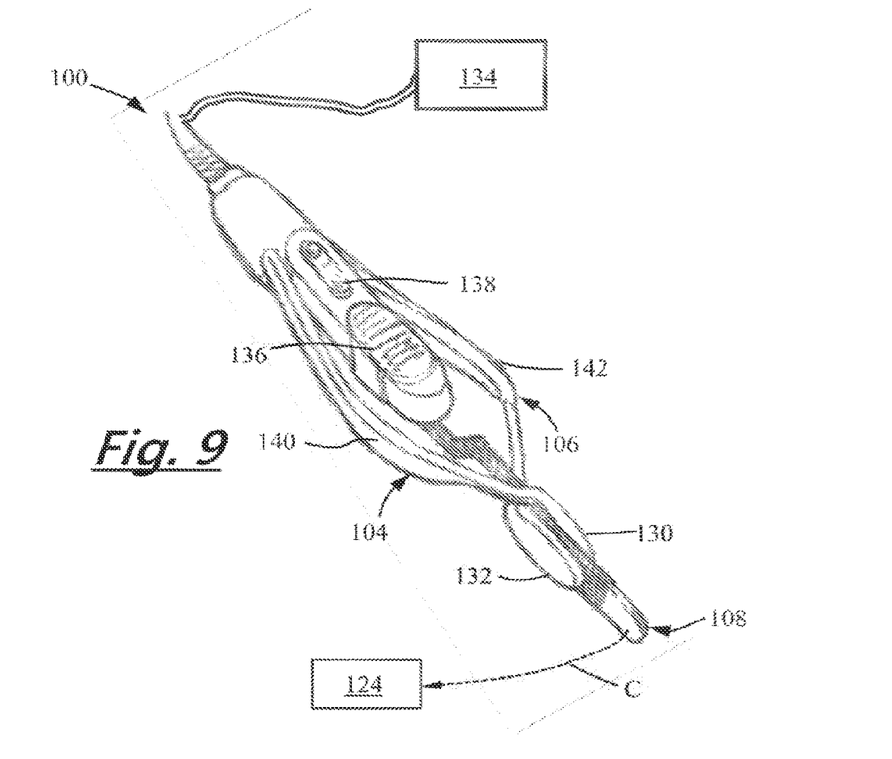
FIG. 9 is a perspective view of an instrument.

The one or more arms may include one or more grippers (See e.g., FIG. 9). The one or more grippers may function to grip or otherwise effect an anatomical feature. The one or more grippers may be conductive so that an electrosurgical signal, therapy or signal can be provided thereto. The one or more grippers may be non-conductive or include portions that are non-conductive. The one or more grippers may include gripping portions having teeth, serrations, or other friction surfaces in order to grip an anatomical feature. The one or more grippers may have paddle type tips. A paddle type tip may be a rectangular tip with corners removed. The one or more grippers may have a tear drop shape that allows the tip to be dug into a surface of an anatomical feature to grasp small bleeders and the larger flats for sealing vessels. An external coating may be applied to the grippers to prevent accidental tissue modification in small, cramped surgical areas. The one or more grippers may have standoffs on internally facing surfaces to prevent shorting during activation of the instrument on small tissue bundles, for example.

The instrument, the effector, or both may include one or more blades. The one or more blades may be configured to and/or may function to effect an object or anatomical feature. The one or more blades may function to deliver one or more therapeutic currents or signals to a surgical site or anatomical feature of interest. The one or more blades may function to manipulate, engage, move, push, pull, cut, tear, coagulate, seal, cauterize, dissect, fulgurate, or a combination thereof an object or anatomical feature. The one or more blades may be any cutting tool, blade, electrode, blade electrode, scalpel, knife, and/or separate member that may be used in or used during a medical or surgical procedure. The one or more blades may be any cutting device that may be extended and retracted between the one or more arms, the effector, or a combination thereof.

The one or more blades may be selectively reciprocated to cut a feature of interest located, gripped, or placed between the arms. The one or more blades may be made of any material that may be sharpened; is strong enough to cut tissue, veins, arteries, an anatomical feature, a feature of interest, or a combination thereof; is biocompatible; may conduct electricity; or a combination thereof. The one or more blades, the distal end of the one or more blades, or both, may conduct energy so that the one or more blades, the distal end, or both can be used as a blade electrode. The distal end of the one or more blades may be blunt. The distal end of the one or more blades may be sharp. The distal end of the one or more blades may be curved, linear, angled, or irregularly shaped. The one or more blades, the distal end of the one or more blades or both may extend beyond a distal end of the arms or other blades when the one or more blades are in a steady state, in a first configuration or in a second configuration. The one or more blades, the distal end of the one or more blades or both may permanently extend beyond a distal end of the gripping assembly.

One or more of the blades may be moveable or reconfigurable. Moveable or reconfigurable may mean that the position of one or more of the blades can be changed. Moveable or reconfigurable may mean that one or more of the blades can be moved or extended away from a hand piece of the instrument, a surgeon or operator using the instrument, one or more arms, blades, electrodes, or a combination thereof. Moveable or reconfigurable may mean that one or more of the blades can be moved or extended towards a patient or surgical site. Moveable may mean that one or more of the blades can be retracted or moved towards a hand piece, a surgeon or operator using the instrument, one or more arms, blades, electrodes, or a combination thereof. Moveable or reconfigurable may mean that one or more of the blades can be vertically moved relative to one or more arms, blades, electrodes, or a combination thereof (e.g., moveable or reconfigurable up and down). Moveable or reconfigurable may mean that one or more of the blades are laterally moveable or displaceable towards or away from one or more arms, blades, electrodes, or a combination thereof (e.g., moveable or reconfigurable side to side). Moveable or reconfigurable may mean that one or more of the blades can be diagonally or along a path that is irregular (e.g., non-linear) relative to one or more arms, blades, electrodes, or a combination thereof (e.g., moveable or reconfigurable up and down). Moveable or reconfigurable may mean that one or more of the blades are rotatable about their longitudinal axis. Moveable may mean that a gap between the arms (e.g., a gap where the blade fits) can be increased, decreased, widened, narrowed, or a combination thereof. Moveable may mean that an outer width of the instrument, effector, or both, from an outside of one arm to an outside of another arm, can be increased, decreased, widened, narrowed, or a combination thereof. Moveable may mean that a gap or distance between a central, longitudinal axis of each arm can be increased, decreased, widened, narrowed, or a combination thereof. Moveable or reconfigurable may mean any combination of blade movements described herein.

The blade may be located between one or more arms, above one or more of the arms, below one or more of the arms, or a combination thereof. The blade may be electrically connected to a power source so that a therapy current or signal can be passed from the power source to the blade or an active portion of the blade, through an object or anatomical feature, to one or more of the arms, and back to the power source. The blade may be electrically connected to a power source so that a therapy current or signal can be passed from the power source to the blade, through an object or anatomical feature, to a remote electrode such as a patient pad. The blade may be connected to a power source, but may be disconnected from the power source and used as a non-electrosurgical scalpel. The blade may be free from any connections to a power source, and may be used as a non-electrosurgical scalpel.

The instrument, the effector, or both may include a connector. The connector may function to connect or maintain a connection between the one or more arms and the blade. The connector may be an insulator. The connector may be insert molded around the blade and the one or more arms. The connector may function to restrict or prevent the one or more arms from moving. The connector may function to provide for the one or more arms or blade to move within a predetermined range.

The instrument, the effector, or both may include one or more scalpels. A scalpel may comprise one scalpel, or one or more scalpels (e.g., two scalpels). The one or more scalpels may be configured to and/or may function to effect an object or anatomical feature. The one or more scalpels may function to deliver one or more therapeutic currents or signals to a surgical site or anatomical feature of interest. The one or more scalpels may function to manipulate, engage, move, push, pull, cut, tear, coagulate, seal, cauterize, dissect, fulgurate, or a combination thereof an object or anatomical feature. The one or more scalpels may be any cutting tool, blade, electrode, blade electrode, scalpel, knife, and/or separate member that may be used in or used during a medical or surgical procedure. The one or more scalpels may be any cutting device that may be extended and retracted between the one or more scalpels, electrodes, or both.

The one or more scalpels may be selectively reciprocated to cut a feature of interest. The one or more scalpels may be made of any material that may be sharpened; is strong enough to cut tissue, veins, arteries, an anatomical feature, a feature of interest, or a combination thereof; is biocompatible; may conduct electricity; or a combination thereof. The one or more scalpels, the distal end of the one or more scalpels, or both, may conduct energy so that the one or more scalpels, the distal end, or both can be used as an electrode. The distal end of the one or more scalpels may be blunt. The distal end of the one or more scalpels may be sharp. The distal end of the one or more scalpels may be curved, linear, angled, or irregularly shaped. The one or more scalpels, the distal end of the one or more scalpels or both may extend beyond a distal end of one or more scalpels in a steady state, in a first configuration or in a second configuration. The one or more scalpels, the distal end of the one or more scalpels or both may permanently extend beyond a distal end of the gripping assembly.

One or more of the scalpels may be moveable or reconfigurable. Moveable or reconfigurable may mean that the position of one or more of the scalpels can be changed. Moveable or reconfigurable may mean that one or more of the scalpels can be moved or extended away from a hand piece of the instrument, a surgeon or operator using the instrument, one or more scalpels, or a combination thereof. Moveable or reconfigurable may mean that one or more of the scalpels can be moved or extended towards a patient or surgical site. Moveable may mean that one or more of the scalpels can be retracted or moved towards a hand piece, a surgeon or operator using the instrument, one or more scalpels, or a combination thereof. Moveable or reconfigurable may mean that one or more of the scalpels can be vertically moved relative to one or more scalpels (e.g., moveable or reconfigurable up and down). Moveable or reconfigurable may mean that one or more of the scalpels are laterally moveable or displaceable towards or away from one or more scalpels (e.g., moveable or reconfigurable side to side). Moveable or reconfigurable may mean that one or more of the scalpels can be diagonally or along a path that is irregular (e.g., non-linear) relative to one or more scalpels (e.g., moveable or reconfigurable up and down). Moveable or reconfigurable may mean that one or more of the scalpels are rotatable about their longitudinal axis. Moveable or reconfigurable may mean any combination of scalpels movements described herein.

A scalpel may be located between one or more other scalpels, above one or more of other scalpels, below one or more other scalpels, or a combination thereof. The one or more scalpels may be electrically connected to a power source so that a therapy current or signal can be passed from the power source to the scalpel, through an object or anatomical feature, to one or more of the arms, and back to the power source. The scalpel may be electrically connected to a power source so that a therapy current or signal can be passed from the power source to the scalpel, through an object or anatomical feature, to a remote electrode such as a patient pad. The scalpel may be free from any connections to a power source, and may be used as a non-electrosurgical scalpel.

The figures of this disclosure illustrate exemplarity instruments and features that are described throughout this disclosure. It is understood that the instruments and features illustrated in the figures are non-exhaustive, and that certain feature described in this disclosure may not be shown in the figures. It is also understood that a feature illustrated in one or more of the figures is not necessary limited to that one particular figure, instrument, and/or embodiment. In other words, it is within the scope of this disclosure that some features, components, and/or instruments illustrated in one or more of the figures of this disclosure can be added, replaced, combined, substituted and/or modified with other features, components, and/or instruments illustrated in other figures of this disclosure and/or described in other sections of this disclosure.

Figure 1A:
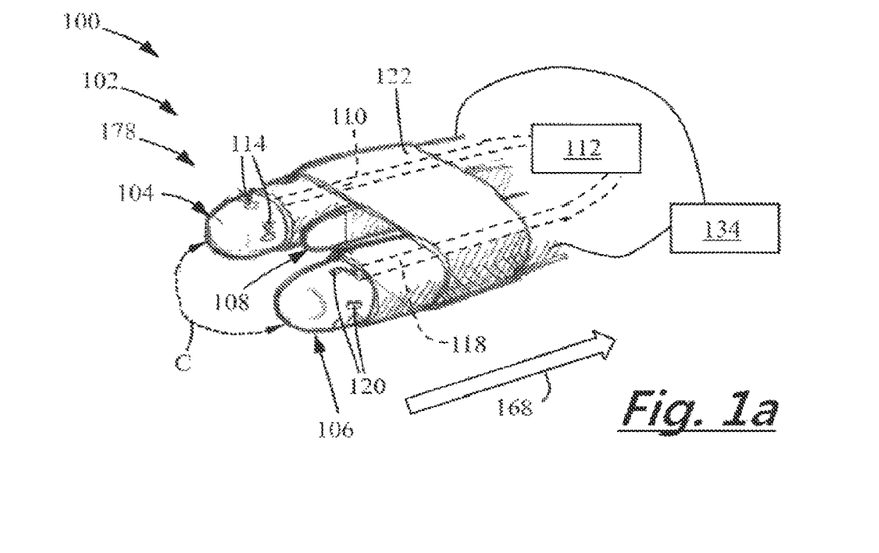
FIG. 1a is a perspective view of an instrument.

FIG. 1a illustrates an instrument 100. The instrument 100 comprises an effector 102 comprising a first arm 104, a second arm 106, and a blade 108. The blade 108 in FIG. 1a is illustrated in a first configuration 178, where the blade 108 is retracted in a direction 168 so that a distal end of the blade 108 does not extend beyond a distal end of the first arm 104 and/or a distal end of the second arm 106. The first arm 104 includes a lumen 110 in communication with a source 112 of fluid. The first arm 104 includes one or more outlets 114 in communication with the lumen 110 for delivering the fluid from the source 112 to at a site of interest, such as a surgical site. The second arm 106 includes a lumen 118 in communication with the source 112. The second arm 106 includes one or more outlets 120 in communication with the lumen 118 for delivering the fluid from the source 120 to the surgical site. The first arm 104 and the second arm 106 are connected together with a connector 122. The first arm 104 and the second arm 106 are connected to a power source 134 so that a therapy current C can be delivered or passed between active portions on the arms 104, 106.

Figure 1B:
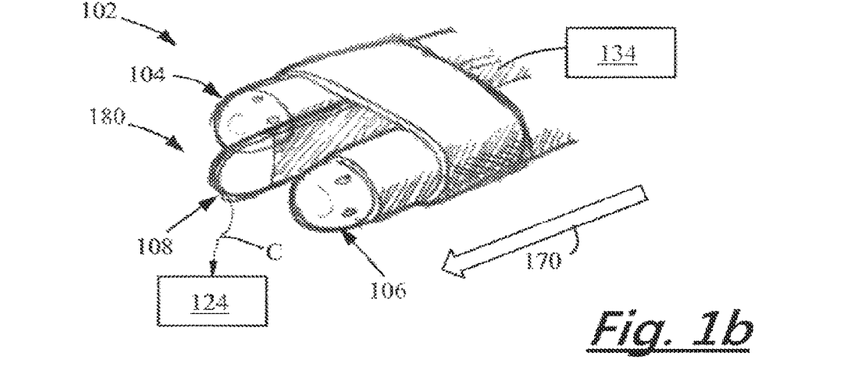
FIG. 1b is a perspective view of an instrument.

FIG. 1b illustrates the effector 102 with the blade 108 in a second configuration 180 where the blade is extended in direction 170 so that a distal end of the blade 108 extends beyond a distal end of the first arm 104 and/or the second arm 106. The blade 108 is connected to a power source 134 so that a therapy current C can be delivered or passed from the power source 134 to the blade 108 and ultimately to a remote electrode 124 or patient pad.

Figure 2:
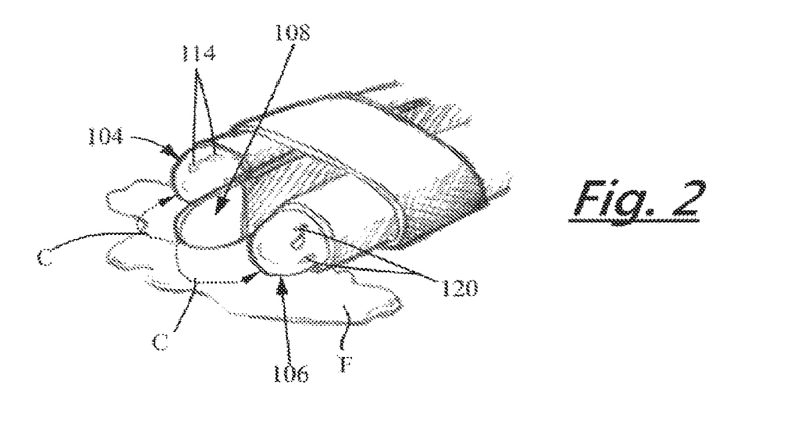
FIG. 2 is a perspective view of an instrument.

FIG. 2 illustrates fluid F delivered to a surgical site from the source 112 (FIG. 1a) via the one or more outlets 114, 120. FIG. 2 also illustrates a therapy current C delivered from the blade 108 to one or both of the arms 104, 106. The therapy current C may travel from the blade 108, through the fluid F and to one or both of the arms 104, 106.

Figure 3:
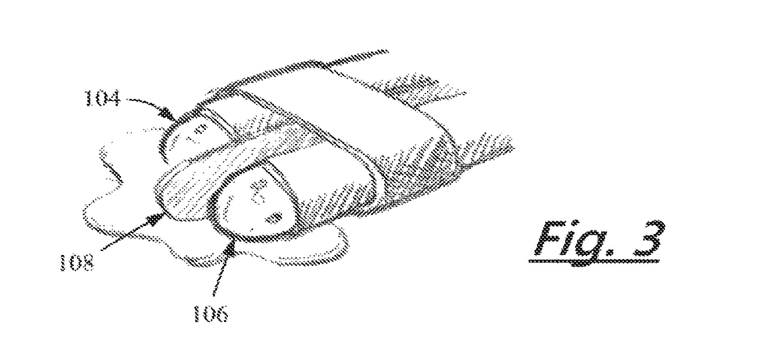
FIG. 3 is a perspective view of an instrument.

FIG. 3 illustrates that one or both of the arms 104, 106 are moveable so that the one or both of the arms 104, 106 can be moved towards the blade 108 as shown, and also away from the blade 108 (c.f. FIG. 2).

Figure 4:
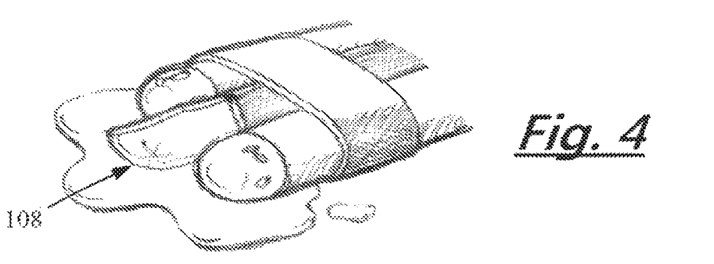
FIG. 4 is a perspective view of an instrument.

FIG. 4 illustrates that the blade 108 can be a non-electrosurgical blade for cutting an object or anatomical feature.

Figure 5:
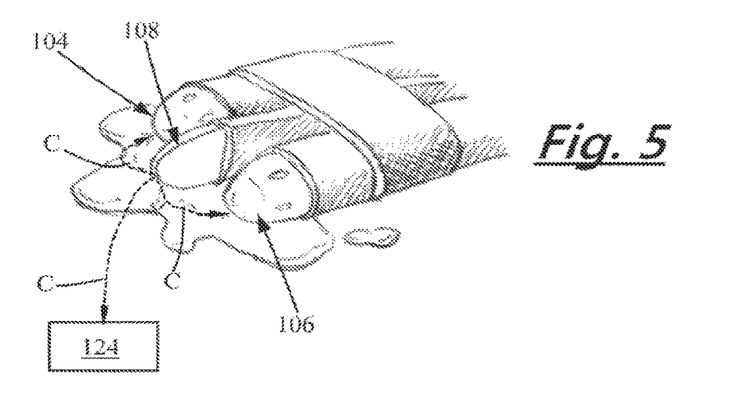
FIG. 5 is a perspective view of an instrument.

FIG. 5 illustrates a therapy current C passing from the blade 108 to a remote electrode 124 or patient pad. A therapy current C can also be passed from the blade 108 to one or both of the arms 104, 106. This may occur in succession (i.e., one after another).

Figure 6:
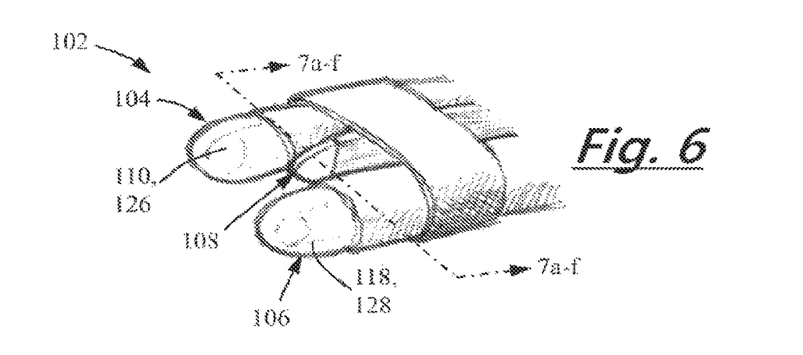
FIG. 6 is a perspective view of an instrument.

FIG. 6 illustrates among the first arm 104 and the second arm 106, the effector 102 includes one or more lumen for delivering irrigation fluid from a source; one or more lumen for delivering suction from a source: one or more lumen including a heat pipe; or a combination thereof. While non-exhaustive, various lumen configurations are illustrated in FIGS. 7a-7f.

Figure 7A:
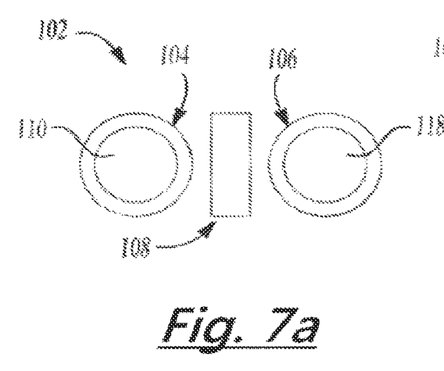
FIG. 7a is a cross-sectional view of the instrument of FIG. 6.

FIG. 7a illustrates a cross section of the effector 102 of FIG. 6 showing the first arm 104, the second arm 106, and the blade 108. The first arm 104 includes a lumen 110, and the second arm 106 includes a lumen 118. Irrigation fluid may be supplied from the source 112 (FIG. 1) to a surgical site through one of the lumen 110, 118 via outlets in the corresponding arm. The other lumen 110, 118 may also be connected to the source 112 for supplying irrigation fluid to the surgical site via outlets in the arm, or the other lumen may include a heat pipe, or may also be connected to the source 112 for supplying suction to the surgical site.

Figure 7B:
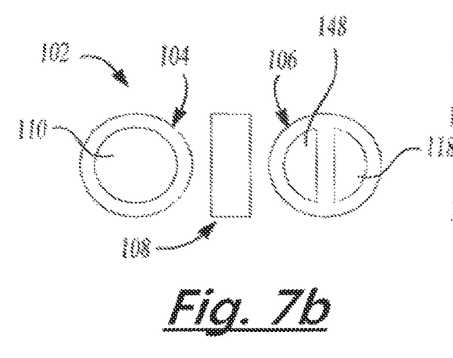
FIG. 7b is a cross-sectional view of the instrument of FIG. 6.

FIG. 7b illustrates the first arm 104 having lumen 110, and the second arm 106 having lumen 118 and lumen 148. Irrigation fluid may be supplied from the source 112 (FIG. 1) to a surgical site through one or more lumen 110, 118, 148 via one or more outlets in the corresponding arm(s). Any remaining lumen 110, 118, 148 may include a heat pipe, or may be connected to the source 112 to supply suction to the surgical site.

Figure 7C:
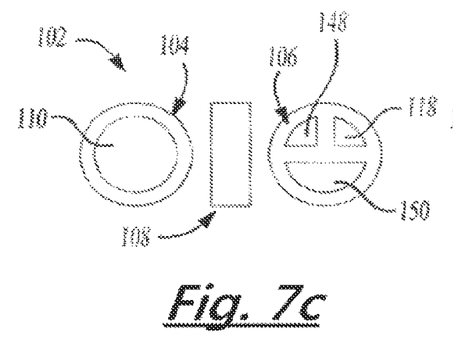
FIG. 7c is a cross-sectional view of the instrument of FIG. 6.

FIG. 7c illustrates the first arm 104 having lumen 110, and the second arm 106 having lumen 118, lumen 148, and lumen 150. Irrigation fluid may be supplied from the source 112 (FIG. 1) to a surgical site through one or more lumen 110, 118, 148, 150 via one or more outlets in the corresponding arm(s). Any remaining lumen 110, 118, 148, 150 may include a heat pipe, or may supply suction to a surgical site from the source 112.

Figure 7D:
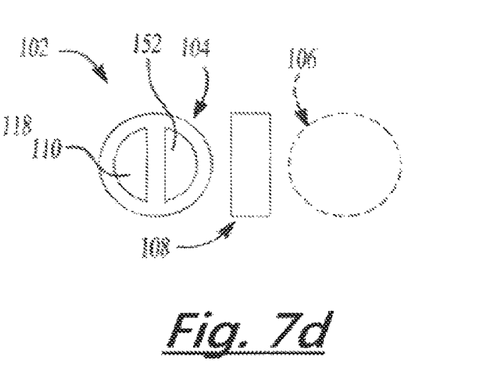
FIG. 7d is a cross-sectional view of the instrument of FIG. 6.

FIG. 7d illustrates the first arm 104 having lumen 110 and 152, and the second arm 106 having any configuration of lumen disclosed herein. Alternatively, the second arm 106 can be free of lumen. Irrigation fluid may be supplied from the source 112 (FIG. 1) to a surgical site through at least one of the lumen 110 and 152. Any remaining lumen 110 and 152 in the first arm 104 and the second arm 106 may include a heat pipe, or may supply suction to a surgical site from the source 112.

Figure 7E:
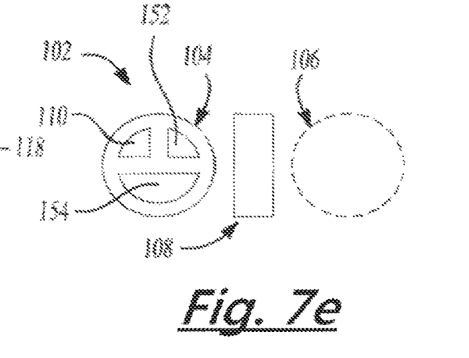
FIG. 7e is a cross-sectional view of the instrument of FIG. 6.
Figure 7F:
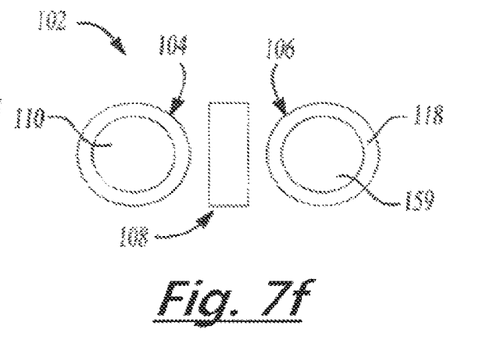
FIG. 7f is a cross-sectional view of the instrument of FIG. 6.

FIG. 7e illustrates the first arm 104 having lumen 110, lumen 152, and lumen 154, and the second arm 106 having any configuration of lumen disclosed herein. Irrigation fluid may be supplied from the source 112 (FIG. 1) to a surgical site through at least one of the lumen 110, 152, and 154. Any remaining lumen 110, 152, and 154 in the first arm 104 and the second arm 106 may include a heat pipe, or may supply suction to the surgical site from the source 112.

Figure 8:
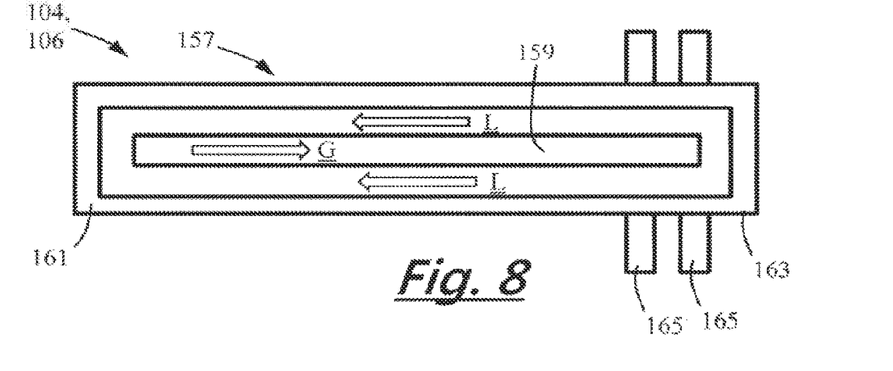
FIG. 8 is a cross-sectional view of an arm including a heat pipe.

FIG. 8 illustrates one of the arms 104, 106 having a heat pipe 157. The heat pipe 157 can be located within or adjacent one or more other lumen containing irrigation fluid and/or suction. The heat pipe 157 includes a scaled lumen 159 having a wick. The lumen 159 is charged with a fluid that can change phase. During use, when an end 161 (e.g., evaporation end; distal end) of the heat pipe 157 is exposed to a heat source, the fluid in the wick evaporates and thus enters the gaseous phase G as it expands and flows towards the second end 163 (e.g., condensation end; proximal end). The second end 163 may be optionally in thermal communication with one or more heat sinks 165 or another type of heat exchanger that draws heat out of the gas G. The gas G then condenses back into a liquid L at the second end 163 and is absorbed by the wick. The liquid L is then wicked back in a direction towards the first end 161 (e.g., evaporation end).

FIG. 9 illustrates an instrument 100. The instrument 100 comprises a first arm 104, a second arm 106, and a blade 108. The first arm includes a first gripper 130, and the second arm 106 includes a second gripper 132. The instrument 100 includes a switch 136 for moving the blade 108 between an extended position and a retracted position. The extended position is illustrated in FIG. 9 where a distal end of the blade 108 is extended beyond a distal end of the first arm 104 the second arm 106. The first arm 104, the second arm 106, and/or the blade 108 may be connected to a power source 134. The instrument 100 includes a switch 138 for supplying a therapy current from the power source 134 to the first arm 104, the first gripper 130, the second arm 106, the second gripper 132, the blade 108, or a combination thereof. A therapy current may be delivered between the first arm 104 and/or first gripper 130 and the second arm 106 and/or second gripper 132. A therapy current C may be delivered from the blade 108 to a remote electrode 124. A therapy current may be delivered from the blade 108 to one or both of the first arm 104 and/or first gripper 130 and the second arm 106 and/or second gripper 132. The first arm 104 includes a first force receiving section 140, and the second arm 106 includes a second force receiving section 142. Applying a force to one or both of the force receiving sections 140, 142 causes the arms 104, 106 and the grippers 130, 132 to separate and move away from each other and from the blade 108.

Figure 10A:
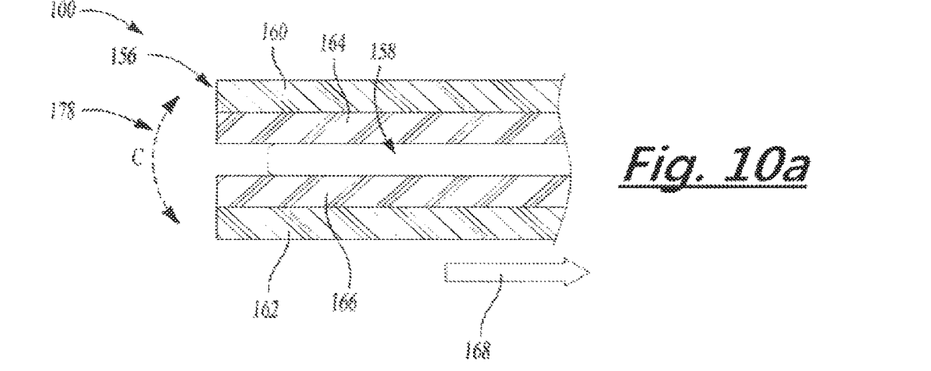
FIG. 10a is a cross-sectional view of an instrument.

FIG. 10a illustrates an instrument 100 comprising a first scalpel 156 and a second scalpel 158. The first scalpel 156 comprises a first electrode 160 and a second electrode 162. A first insulator 164 is located between the first electrode 160 and the second scalpel 158 so that the first electrode 160 is electrically insulated from the second scalpel 158. A second insulator 166 is located between the second electrode 162 and the second scalpel 158 so that the second electrode 162 is electrically insulated from the second scalpel 158. The second scalpel 158 is illustrated in a first configuration 178 where the second scalpel 158 is retracted in a direction 168 so that a distal end of the second scalpel 158 does not extend beyond a distal end of the first and second electrodes 160, 162. A therapy current C supplied by a source 134 (FIG. 1) can be passed between the first and second electrodes 160, 162.

Figure 10B:
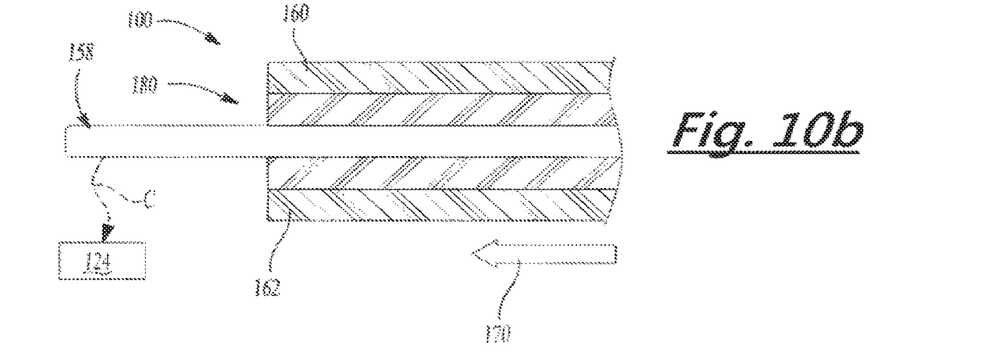
FIG. 10b is a cross-sectional view of an instrument.

FIG. 10b illustrates an instrument 100 where the second scalpel 158 is in a second configuration 180. In the second configuration 180, the second scalpel 158 is extended in a distal direction 170 so that a distal end of the second scalpel 158 extends beyond a distal end of the first and second electrodes 160, 162. A therapy current C supplied by a source 134 (FIG. 1) can be passed between the second scalpel 158 and a remote electrode 124.

Figure 10C:
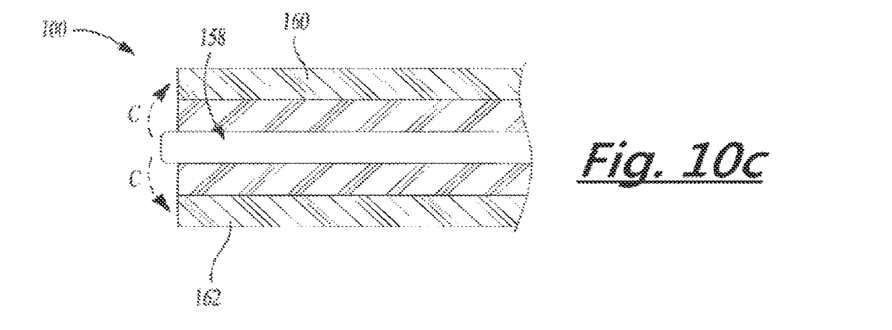
FIG. 10c is a cross-sectional view of an instrument.

FIG. 10c illustrates an instrument 100 where the second scalpel 158 is positioned relative to the first and second electrodes 160, 162 so that a therapy current C supplied by a source 134 (FIG. 1) can be passed between the second scalpel 158 and the electrodes 160, 162.

Figure 10D:
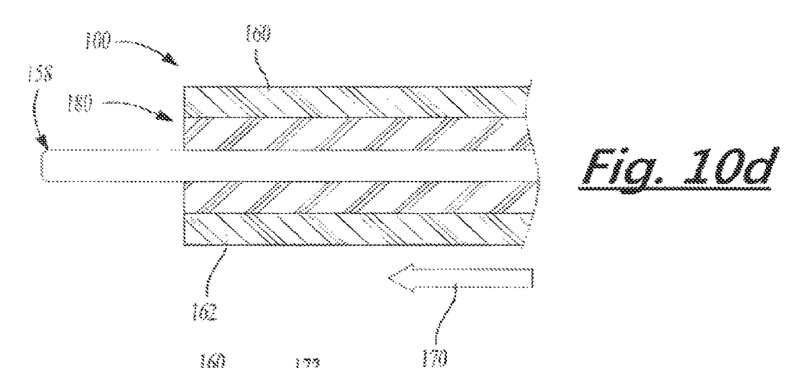
FIG. 10d is a cross-sectional view of an instrument.
Figure 10E:
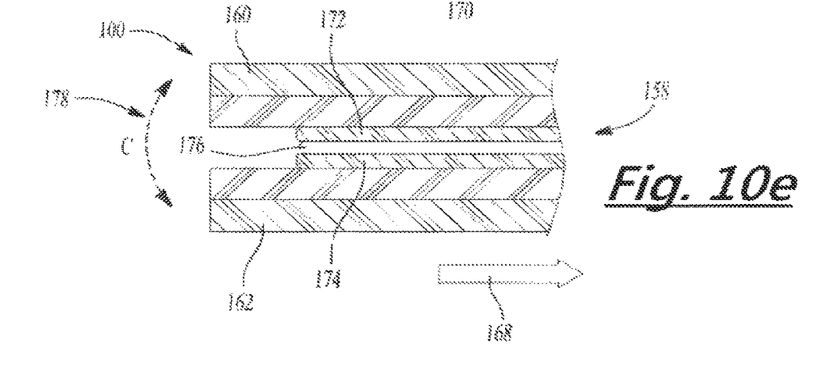
FIG. 10e is a cross-sectional view of an instrument.

FIG. 10d illustrates the second scalpel 158 in the second configuration beyond a distal end of the first and second electrodes 160, 162. The second scalpel can be a non-electrosurgical blade for cutting an object or anatomical feature, FIG. 10e illustrates a second scalpel 158 comprising a first electrode 172 and a second electrode 174. An insulator 176 separates the electrodes 172, 174. The second scalpel 158 is illustrated in a first configuration 178 where the second scalpel 158 is retracted in a proximal direction 168 so that a distal end of the second scalpel 158 does not extend beyond a distal end of the electrodes 160, 162. A therapy current C supplied by a source 134 (FIG. 1) can be passed between the first and second electrodes 160, 162.

Figure 10F:
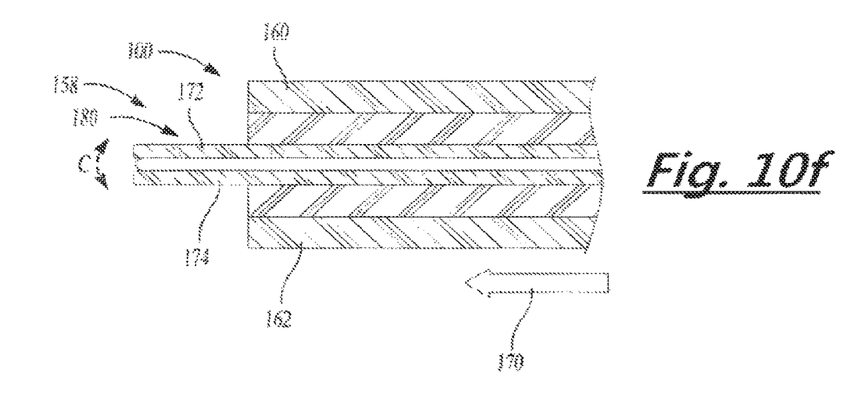
FIG. 10f is a cross-sectional view of an instrument.

FIG. 10f illustrates the second scalpel 158 in a second configuration 180 where the second scalpel 158 is extended in a distal direction 170 so that a distal end of the second scalpel 158 extends beyond a distal end of the electrodes 160, 162. A therapy current C can be passed between the first and second electrodes 172, 174.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc, are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner. As can be seen, the teaching of amounts expressed as "parts by weight" herein also contemplates the same ranges expressed in terms of percent by weight. Thus, an expression in the Detailed Description of the Teachings of a range in terms of at "'x' parts by weight of the resulting polymeric blend composition" also contemplates a teaching of ranges of same recited amount of "x" in percent by weight of the resulting polymeric blend composition."

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

The invention claimed is:

1. An instrument comprising:
a first arm extending from a proximal end to a distal end, the first arm including a lumen configured to be in communication with a source of irrigation fluid, the distal end of the first arm including one or more fluid outlets in communication with the lumen for delivering the irrigation fluid from the source to a surgical site;
a second arm spaced laterally from the first arm and extending from a proximal end to a distal end; and
a blade;
wherein the instrument is switchable between a first configuration and a second configuration;
wherein in the first configuration, the instrument is configured to deliver a first therapy current through the distal end of the first arm, the distal end of the second arm, or both; and
wherein in the second configuration, a distal end of the blade extends beyond the distal end of the first arm and beyond the distal end of the second arm.

2. The instrument of claim 1, wherein the blade is disposed between an external surface of the first arm and an external surface of the second arm.

3. The instrument of claim 2, wherein the blade is configured to move proximally and distally relative to the first and second arms.

4. The instrument of claim 3, wherein in the first configuration, a distal end of the blade is retracted proximal to the distal end of the first arm and proximal to the distal end of the second arm.

5. The instrument of claim 3, wherein the second configuration is a monopolar electrosurgical configuration where a second therapy current is delivered from the blade to a remote electrode.

6. The instrument of claim 5, wherein one or both of the first arm and the second arm are moved towards the blade in the second configuration.

7. The instrument of claim 3, wherein the second configuration is a bipolar electrosurgical configuration where a second therapy current is delivered between the blade and one or both of the first arm and the second arm.

8. The instrument of claim 1, wherein the blade is an electrosurgical blade.

9. The instrument of claim 1, wherein the blade is a non-electrosurgical scalpel.

10. The instrument of claim 1, wherein the first arm extends generally parallel to the second arm.

11. The instrument of claim 1, wherein the second arm includes a lumen configured to be in communication with the source of irrigation fluid, and wherein the second arm includes one or more outlets in communication with the lumen of the second arm for delivering the irrigation fluid to the surgical site.

12. An instrument comprising:
a forceps comprising:
a first arm having a first gripper, a first force receiving section, a lumen configured to be in communication with a source of irrigation fluid, and one or more fluid outlets in communication with the lumen for delivering the irrigation fluid from the source to a surgical site;
a second arm having a second gripper and a second force receiving section; and
a blade configured to move proximally and distally relative to the first and second arms;
wherein the first arm and the second arm cross over one another; and
wherein applying a first force to the first force receiving section in a first direction and applying a second force to the second force receiving section in an opposite second direction causes the first gripper and the second gripper to separate;
wherein the instrument is switchable between a first configuration and a second configuration;
wherein in the first configuration, the instrument is configured to deliver a first therapy current through the first arm, the second arm, or both; and
wherein in the second configuration, the blade extends beyond a distal end of the first arm and beyond a distal end of the second arm.

13. The instrument of claim 12, wherein the blade is disposed between an external surface of the first arm and an external surface of the second arm.

14. The instrument of claim 12, wherein in the first configuration, the blade is proximally retracted relative to the distal end of the first arm and the distal end of the second arm.

15. The instrument of claim 12, wherein the second configuration is a monopolar electrosurgical configuration where a second therapy current is delivered from the blade to a remote electrode.

16. The instrument of claim 12, wherein the second configuration is a bipolar electrosurgical configuration where a second therapy current is delivered between the blade and one or both of the first arm and the second arm.

17. The instrument of claim 12, wherein the blade is arranged substantially parallel to the first gripper and to the second gripper.

18. An instrument comprising:
a first arm extending from a proximal end to a distal end, the first arm including a lumen configured to be in communication with a source of irrigation fluid, the distal end of the first arm including one or more fluid outlets in communication with the lumen for delivering the irrigation fluid from the source to a surgical site;
a second arm extending from a proximal end to a distal end, wherein the second arm is spaced laterally from the first arm and extends generally parallel to the first arm; and
a blade disposed between an external surface of the first arm and an external surface of the second arm;
wherein the instrument is switchable between a first configuration and a second configuration;
wherein in the first configuration, the instrument is configured to deliver a first therapy current through the distal end of the first arm, the distal end of the second arm, or both; and
wherein in the second configuration, a distal end of the blade extends beyond the distal end of the first arm and beyond the distal end of the second arm.

19. The instrument of claim 18, wherein the blade is configured to move proximally and distally relative to the first and second arms.

20. The instrument of claim 19, wherein in the first configuration, the blade is proximally retracted relative to the distal end of the first arm and the distal end of the second arm.

* * * * *